United States Patent [19]

Halenbeck et al.

[11] Patent Number: 4,931,543
[45] Date of Patent: Jun. 5, 1990

[54] PROCESS FOR RECOVERING MICROBIALLY PRODUCED INTERLEUKIN-2

[75] Inventors: Robert Halenbeck, San Rafael; Flint Smith; Michael Kunitani, both of Oakland, all of Calif.

[73] Assignee: Cetus Corporation, Emeryville, Calif.

[21] Appl. No.: 167,145

[22] Filed: Mar. 25, 1988

Related U.S. Application Data

[63] Continuation-in-part of Ser. No. 48,405, May 11, 1987, abandoned.

[51] Int. Cl.$^5$ .............................................. C07K 3/28
[52] U.S. Cl. .................................... 530/351; 530/402; 530/408; 530/409; 530/410; 530/412; 530/416; 530/417; 530/422; 530/424; 530/825; 435/69.52
[58] Field of Search ............... 530/351, 412, 416, 417, 530/422, 424, 402, 408–410, 825; 435/68, 70

[56] References Cited

U.S. PATENT DOCUMENTS

| | | | |
|---|---|---|---|
| 4,464,295 | 8/1984 | Bhadwri et al. | 530/350 |
| 4,476,049 | 10/1984 | Kung | 435/948 |
| 4,490,289 | 12/1984 | Stern | 435/68 |
| 4,511,502 | 4/1985 | Builder et al. | 435/68 |
| 4,511,503 | 4/1985 | Builder et al. | 435/68 |
| 4,512,922 | 4/1985 | Jones et al. | 435/68 |
| 4,518,526 | 5/1985 | Olson | 435/68 |
| 4,518,584 | 5/1985 | Mark et al. | 435/68 |
| 4,530,787 | 7/1985 | Shaked | 530/351 |
| 4,569,790 | 2/1986 | Koths | 530/351 |
| 4,572,798 | 2/1986 | Koths et al. | 530/351 |
| 4,599,197 | 7/1980 | Wetzel | 435/68 |
| 4,604,377 | 9/1986 | Fernandes et al. | 435/68 |
| 4,620,948 | 11/1986 | Builder et al. | 435/68 |
| 4,656,255 | 4/1987 | Seely | 435/68 |
| 4,659,568 | 4/1987 | Heilman | 435/68 |
| 4,677,196 | 6/1987 | Raisch et al. | 530/416 |
| 4,748,234 | 5/1988 | Darin | 530/412 |
| 4,766,205 | 8/1988 | Ghosh-Dastilar | 435/68 |
| 4,766,224 | 8/1988 | Rausch | 435/68 |
| 4,797,474 | 1/1987 | Patroni et al. | 530/417 |
| 4,801,691 | 1/1989 | Amer | 530/417 |

FOREIGN PATENT DOCUMENTS

| | | |
|---|---|---|
| 114506 | 8/1984 | European Pat. Off. |
| 145390 | 6/1985 | European Pat. Off. |
| 147819 | 7/1985 | European Pat. Off. |
| 158487 | 10/1985 | European Pat. Off. |
| 208539 | 1/1987 | European Pat. Off. |
| 215658 | 3/1987 | European Pat. Off. |
| 225156 | 6/1987 | European Pat. Off. |
| 268110 | 5/1988 | European Pat. Off. |
| WO85/05637 | 12/1985 | PCT Int'l Appl. |
| WO86/05809 | 10/1986 | PCT Int'l Appl. |
| WO88/08003 | 10/1988 | PCT Int'l Appl. |
| WO88/08849 | 11/1988 | PCT Int'l Appl. |
| WO86/06385 | 11/1986 | World Int. Prop. O. |

OTHER PUBLICATIONS

Sofer et al, *Bio Technique*, Nov./Dec. 1983, pp. 198–203.
AUA 43070, 1985 Australian Abstract.
Baldwin, R. L. et al., Ann. Rev. Biochem., pp. 453–475 (1975).
Weber, K. et al., J. Biol. Chem., vol. 246:4504–4509 (1971).
Light, A., Biotechniques, vol. 3:298–306.
Weir, M. et al., Symposium on HPLC of Proteins, West Germany, Oct. 1986.

(List continued on next page.)

*Primary Examiner*—Garnette D. Draper
*Attorney, Agent, or Firm*—Lisabeth F. Murphy; Philip L. McGarrigle; Albert P. Halluin

[57] ABSTRACT

A process for recovering substantially pure rIL-2 from transformed microorganisms in which the cells are disrupted, impure insoluble rIL-2 is separated from the bulk of the cellular components, the separated impure rIL-2 is solubilized and partially purified in a reduced form, the solubilized rIL-2 is oxidized, the oxidized rIL-2 is purified to clinically acceptable levels, and the oxidized, purified IL-2 is denatured by placing it into a solution of a chaotropic agent, solids are removed from the solution and rIL-2 is renatured from the solution.

17 Claims, 5 Drawing Sheets

Cells Containing rIL-2

1. concentration by cross-flow filtration
2. cell disruption
3. diafiltration against deionized $H_2O$
4. redisruption
5. sucrose added to final p = 1.1–1.25
6. centrifuge (high speed)

particle pellet (refractile bodies) / supernatant (discard)

solubilize and reduce with SDS/DTT remove reducing agent by gel filtration oxidize rIL-2 purify rIL-2 by RP-HPLC precipitate rIL-2, recover paste 1. denature rIL-2 with chaotropic agent
2. filter/centrifuge solids (discard) / solution containing denatured rIL-2 renature rIL-2

OTHER PUBLICATIONS

Liang, S. M. et al., Biochem. J., vol. 229:429–439 (1985).
Kato, K. et al., Biochem. Biophys., Res. Comm., vol. 130:692–699 (1985).
Winkler, M. R., Biotechnology, vol. 3:990–999 (1985).
Hermann, R. et al., Biochem., vol. 24:1817–1821 (1985).
Hermann, R. et al., J. Biol. Chem., vol. 258:11014–11019 (1983).
Boss, M. A. et al., Nucl. Acids Res., vol. 12:3791–3806 (1984).
Cabilly, S., Proc. Natl. Acad. Sci. USA, vol. 81:3273–3277 (1984).
Pigiet, V. P., Proc. Natl. Acad. Sci. USA, vol. 83:7643–7647 (1986).
Tietze, F., Anal. Biochem., vol. 27:502 (1969).
Kawaguchi, Y. et al., J. Biotechnol., vol. 1:307–315 (1984).
Marston, F. A. O. et al., Biotechnol., 800–804 (1984).
Tsuji, T. et al., Biochem., vol. 26:3129–3134 (1987).
Means, G. E. et al., Chem. Modif. of Proteins, Holden Day, pp. 221–222.
Becker, T. et al., Biotech. Advs., vol. 1:247–261 (1983).
Kleid, D. G. et al., Devel. in Indust. Microbiol., vol. 25:317–325 (1983).
Jaenicke, R. et al., Meth. in Enzymol., vol. 131:218–250 (1986).
Sofer, G. et al., BioTechnology, vol. 2:1035–1038 (1986).

PROCESS FOR RECOVERING MICROBIALLY PRODUCED INTERLEUKIN-2

DESCRIPTION

1. Cross-Reference to Related Application

This application is a continuation-in-part of copending U.S. Ser. No. 048,405, filed 11 May 1987 now abandoned.

2. Technical Field

This invention is in the field of biochemical engineering. More particularly, the invention concerns an improved biochemical separation or recovery process in which recombinant interleukin-2 (rIL-2) is recovered in substantially pure form from the transformed microorganisms in which it is made and then renatured.

3. Background

IL-2, a lymphokine which is produced by normal peripheral blood lymphocytes and induces proliferation of antigen- or mitrogen-stimulated T cells after exposure to plant lectins, antigens, or other stimuli, was first described by Morgan, D. A., et al, *Science* (1976) 193:1007-1008. Then called T cell growth factor because of its ability to induce proliferation of stimulated T lymphocytes, it is now recognized that in addition to its growth factor properties it modulates a variety of functions of immune system cells in vitro and in vivo and has been renamed IL-2. IL-2 is one of several lymphocyte-produced messenger-regulatory molecules that mediate immunocyte interactions and functions.

IL-2 was initially made by cultivating human peripheral blood lymphocytes (PBL) or other IL-2-producing cell lines. See, for instance, U.S. Pat. No. 4,401,756. Recombinant DNA technology has provided an alternative to PBLs and cell lines for producing IL-2. Taniguchi, T., et al, *Nature* (1983) 302:305-310 and Devos, R., *Nucleic Acids Research* (1983) 11:4307-4323 have reported cloning the human IL-2 gene and expressing it in microorganisms.

Native human IL-2 is an antigen-nonspecific, genetically unrestricted soluble factor produced by erythrocyte rosette positive T cells stimulated with antigens, mitogens or alloantigens. It is a protein with a reported molecular weight in the approximate range of 13,000 to 17,000 daltons (S. Gillis and J. Watson, *J Exp Med* (1980) 159:1709) and an isoelectric point in the approximate range of pH 6-8.5. Human IL-2 has a number of in vitro and in vivo effects including enhancing the proliferative responses of human peripheral blood mononuclear cells or murine thymocytes, enhancing the immune response in humans and in animals against bacterial, parasitic, fungal, protozoan and viral infections, and supporting the growth of continuous T cell lines.

rIL-2 has been obtained from genetically engineered *E. coli* as an unglycosylated protein with biological activities equivalent to those of native, glycosylated IL-2. Devos et al., *Nucleic Acid Research* (1983) 11:4307-4323; Rosenberg et al, *Science* (1984) 223:1412-1415; Wang et al, *Science* (1984) 224:1431-1433; and Doyle et al, *J. Biol Resp Modifiers* (1985) 4:96-109). Rosenberg and his coworkers have shown that systemic administration of rIL-2 in high doses causes regression of established metastatic cancers in mice (Rosenberg et al, *J Exp Med* (1985) 161:1169-1188); and, in conjunction with lymphokine-activated killer cells (Rosenberg et al, *New Eng J Med* (1985) 313:1485-1492) and tumorinfiltrating lymphocytes (Rosenberg, et al *Science* (1986) 233:1318-1321), in humans.

U.S. Pat. No. 4,518,584 discloses recombinant muteins (analogs) of IL-2 in which the cysteine normally occurring at position 125 of the wild-type or native molecule has been replaced with a neutral amino acid, such as serine or alanine. European Patent (EP) publication 200,280, published 10 Dec. 1986 discloses rIL-2 muteins wherein the methionine at position 104 has been replaced by a conservative amino acid.

Microbially produced rIL-2 is not glycosylated and is produced in a denatured state. It is insoluble and, when expressed at high levels, it precipitates intracellularly in the form of "refractile" or "inclusion" bodies which appear as bright spots visible within the enclosure of the cell under a phase contrast microscope at magnifications down to 1000 fold.

The heretofore available methods for recovering microbially produced rIL-2 from the organisms that produce it are described below.

U.S. Pat. No. 4,569,790 describes a process for recovering rIL-2 from an rIL-2-producing microorganism in which the cell is disrupted, non rIL-2 proteins are extracted selectively from the disruptate using an aqueous solution of a chaotropic agent such as urea, the rIL-2 is solubilized with a surfactant, e.g., sodium dodecyl sulfate (SDS), solution containing a reducing agent, the reducing agent is removed from the solution, the rIL-2 is subjected to a controlled oxidation, and the oxidized rIL-2 is purified by a combination of RP-HPLC and gel filtration steps. The process of the present invention employs a variation of the process of this patent and includes a renaturation step following the RP-HPLC purification step to provide renatured rIL-2 that has higher specific activity, improved water solubility and stability and may be less antigenic relative to the material produced by the patented process.

Commonly owned U.S. Pat. Nos. 4,530,787 and 4,572,798 describe techniques for carrying out the controlled oxidation step referred to above. The former patent uses o-iodosobenzoic acid as an oxidizing agent and the latter uses $Cu^{+2}$ cation as an oxidation promoter.

EP publication 206,828, published 30 Dec. 1986, and entitled "Process for Recovering Refractile Bodies Containing Heterologous Proteins from Microbial Hosts" disclose methods for recovering and purifying refractile bodies of rIL-2 from *E. coli*. To isolate the refractile material, the processes initially involve disrupting the cell wall and membrane of the host cell, removing greater than 99% by weight of the salts from the disruptate, redisrupting the desalted disruptate, adding a material to the disruptate to create a density or viscosity gradient in the liquid within the disruptate, and separating the refractile material from the cellular debris by high-speed centrifugation. The rIL-2 is then solubilized with a solubilizing agent such as SDS, chromatographed to remove high molecular weight contaminants, oxidized, and purified by RP-HPLC, ultrafiltration, and gel filtration. The process of the present invention is also a variation of the process described in this copending application.

An abstract titled "Purification and Renaturation of Recombinant Interleukin-2" presented at the 6th International Symposium on HPLC of Proteins, Peptides and Polynucleotides at Baden-Baden, West Germany in Oct. 1986 describes a process in which rIL-2 is solubilized from inclusion bodies with 6M guanidine hydrochloride/10 mM dithiothreitol (DTT) and purified in a reduced, denatured form by FPLC gel permeation. The solution from the FPLC gel permeation is diluted to effect renaturation and autooxidation. In this regard U.S. Pat. Nos. 4,511,502; 4,511,503; 4,512,922 and 4,518,526; and EP publication 114,506 describe a similar procedure for recovering heterologous proteins in general from refractile bodies. In such processes, the oxidation and renaturation of the recombinant protein are carried out in a single step.

EP publication 145,390 describes a process for recovering rIL-2 from *E. coli* in which the cells are suspended in 7M guanidine hydrochloride, solids are removed by centrifugation, the rIL-2-containing supernatant is dialyzed to remove the guanidine hydrochloride and the dialyzate is purified by anion exchange chromatography, gel filtration and RP-HPLC.

DISCLOSURE OF THE INVENTION

The invention is an improvement in a process for recovering rIL-2 from transformed microorganisms containing the rIL-2 wherein the rIL-2 is separated from the bulk of the cellular components of the microorganisms, solubilized in a reduced form, thereafter oxidized, and thereafter purified to clinically acceptable purity and endotoxin levels. The improvement comprises denaturing the oxidized, purified rIL-2 by placing the rIL-2 in a solution of a chaotropic agent, removing solids from the solution, and thereafter renaturing the rIL-2 from the solution whereby a renatured, oxidized, purified rIL-2 having improved stability and water solubility properties in the absence of detergents is obtained.

Another aspect of this invention is the renatured, oxidized, purified rIL-2 that is prepared by the above described improved process.

MODES FOR CARRYING OUT THE INVENTION

A. Definitions

Figure 1:
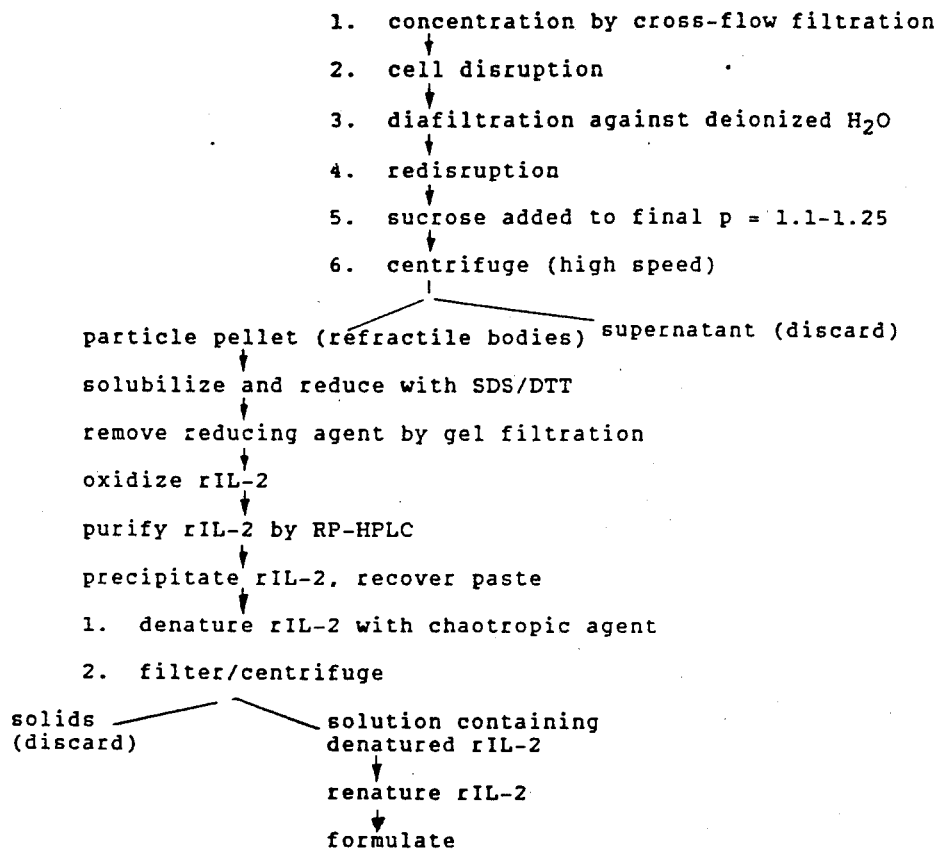
FIG. 1 is a flow diagram of the preferred embodiment of the invention process.

As used herein, the term "rIL-2" refers to recombinant interleukin-2 or interleukin-2-like polypeptides produced by a transformed microorganism and whose amino acid sequence is the same as or similar or substantially homologous to the unglycosylated and/or glycosylated native interleukin-2. Examples of such rIL-2s are those described in European published patent applications 91,539, 88,195, and 109,748, as well as those described in U.S. Pat. No. 4,518,584, EP publication 200,280, and bovine IL-2 as described by Cerretti et al, *Proc Natl Acad Sci USA* (1986) 83:3223–3227. The disclosures of all these references are incorporated herein by reference.

The IL-2s particularly preferred herein are those biologically active muteins (analogs) of human IL-2 in which amino acid residues not essential to biological activity have been deliberately deleted or replaced with a conservative amino acid as indicated below. More specifically, preferred IL-2s include those wherein the cysteine residue at position 125 is replaced with another amino acid, preferably neutral or conservative, to eliminate sites for intermolecular crosslinking or incorrect intramolecular disulfide and, optionally, the N-terminal alanine residue of the native counterpart is eliminated. As used herein, such neutral or conservative amino acids are glycine, serine, valine, alanine, leucine, isoleucine, tyrosine and methionine. More particularly, preferred IL-2 muteins in the formulations of this invention are those wherein (1) the cysteine residue at amino acid position 125 of the native counterpart is replaced by a serine residue (designated IL-$2_{ser125}$) or alanine residue (designated IL-$2_{ala125}$); or (2) the initial alanine residue is eliminated and the cysteine at position 125 is replaced by serine (designated des-alanyl-IL-$2_{ser125}$).

Other IL-2s particularly preferred herein are those biologically active muteins described in European Patent Publication 200,280 wherein oxidation-susceptible methionine residues are replaced with a neutral or conservative amino acid, a preferred mutein includes replacing the methionine at position 104 with a conservative amino acid such as alanine.

EP 200,280 also describes amino-terminal deletions of IL-2 wherein one or more of the first six amino acids are deleted. Preferred oxidation-resistant muteins include ala$_{104}$ser$_{125}$IL-2, ala$_{104}$IL-2, ala$_{104}$ala$_{125}$IL-2, val$_{104}$ser$_{125}$IL-2, val$_{104}$IL-2, val$_{104}$ala$_{125}$IL-2, des-ala$_1$ala$_{104}$ser$_{125}$IL-2, des-ala$_1$ala$_{104}$IL-2, des-ala$_1$ala$_{104}$ala$_{125}$IL-2, des-ala$_1$val$_{104}$ser$_{125}$IL-2, des-ala$_1$val$_{104}$IL-2, des-ala$_1$val$_{104}$ala$_{125}$IL-2, des-ala$_1$des-pro$_2$ala$_{104}$ser$_{125}$IL-2, des-ala$_1$des-pro$_2$ala$_{104}$IL-2, des-ala$_1$des-pro$_2$ala$_{104}$ala$_{125}$IL-2, des-ala$_1$des-pro$_2$val$_{104}$ser$_{125}$IL-2, des-ala$_1$des-pro$_2$val$_{104}$IL-2, des-ala$_1$des-pro$_2$val$_{104}$ala$_{125}$IL-2, des-ala$_1$des-pro$_2$des-thr$_3$ala$_{104}$ser$_{125}$IL-2, des-ala$_1$des-pro$_2$des-thr$_3$ala$_{104}$IL-2, des-ala$_1$des-pro$_2$-des-thr$_3$ala$_{104}$ala$_{125}$IL-2, des-ala$_1$des-pro$_2$des-thr$_3$-val$_{104}$ser$_{125}$IL-2, des-ala$_1$des-pro$_2$des-thr$_3$val$_{104}$IL-2, des-ala$_1$des-pro$_2$des-thr$_3$val$_{104}$ala$_{125}$IL-2, des-ala$_1$des-pro$_2$des-thr$_3$des-ser$_4$ala$_{104}$ser$_{125}$IL-2, des-ala$_1$des-pro$_2$des-thr$_3$des-ser$_4$ala$_{104}$IL-2, des-ala$_1$des-pro$_2$des-thr$_3$des-ser$_4$ala$_{104}$ala$_{125}$IL-2, des-ala$_1$des-pro$_2$des-thr$_3$des-ser$_4$val$_{104}$ser$_{125}$IL-2, des-ala$_1$des-pro$_2$des-thr$_3$des-ser$_4$val$_{104}$IL-2, des-ala$_1$des-pro$_2$des-thr$_3$des-ser$_4$val$_{104}$ala$_{125}$IL-2, des-ala$_1$des-pro$_2$des-thr$_3$des-ser$_4$des-ser$_5$ala$_{104}$ser$_{125}$IL-2, des-ala$_1$des-pro$_2$des-thr$_3$des-ser$_4$des-ser$_5$ala$_{104}$IL-2, des-ala$_1$des-pro$_2$des-thr$_3$des-ser$_4$des-ser$_5$ala$_{104}$ala$_{125}$-IL-2, des-ala$_1$des-pro$_2$des-thr$_3$des-ser$_4$des-ser$_5$val$_{104}$-ser$_{125}$IL-2, des-ala$_1$des-pro$_2$des-thr$_3$des-ser$_4$des-ser$_5$-val$_{104}$IL-2, des-ala$_1$des-pro$_2$des-thr$_3$des-ser$_4$des-ser$_5$-val$_{104}$-ala$_{125}$IL-2, des-ala$_1$des-pro$_2$des-thr$_3$des-ser$_4$-des-ser$_5$des-ser$_6$ala$_{104}$ala$_{125}$IL-2, des-ala$_1$des-pro$_2$-des-thr$_3$des-ser$_4$des-ser$_5$des-ser$_6$ala$_{104}$IL-2, des-ala$_1$des-pro$_2$des-thr$_3$-des-ser$_4$des-ser$_5$des-ser$_6$ala$_{104}$ser$_{125}$IL-2, des-ala$_1$des-pro$_2$des-thr$_3$des-ser$_4$des-ser$_5$-des-ser$_6$val$_{104}$ser$_{125}$IL-2, des-ala$_1$des-pro$_2$des-thr$_3$-des-ser$_4$des-ser$_5$des-ser$_6$val$_{104}$IL-2, or des-ala$_1$des-pro$_2$des-thr$_3$des-ser$_4$des-ser$_5$des-ser$_6$val$_{104}$-ala$_{125}$IL-2.

Other amino-terminal deletions of IL-2 are disclosed in *Chemical Abstracts* (1987) 106:(21):170236f, an abstract of Japanese Patent Publication No. 61/225199, published 6 Oct. 1986, wherein any one of the first 15 amino acids of IL-2 are deleted. PCT 87/04714, published 13 Aug. 1987 describes deletions or replacements of one or more of the amino acid residues in positions 2 to 11 and/or 128 to 133 from the amino-terminal alanine of IL-2.

The precise chemical structure of the rIL-2 will depend on a number of factors. As ionizable amino and carboxyl groups are present in the molecule, a particular rIL-2 may be obtained as an acidic or basic salt, or in neutral form. All such preparations which retain their activity when placed in suitable environmental conditions are included in the definition of "rIL-2." Further, the primary amino acid sequence of the protein may be augmented by derivatization using sugar moieties (glycosylation) or by other supplementary molecules such as lipids, phosphate, acetyl groups and the like, more commonly by conjugation with saccharides. Certain aspects of such augmentation are accomplished through post-translational processing systems of the producing host; other such modifications may be introduced in vitro. In any event, such modifications are included in the definition of rIL-2 herein so long as the activity of the protein, as defined above, is not destroyed. It is expected, of course, that such modifications may quantitatively or qualitatively affect biological activity, either by enhancing or diminishing the activity of the protein in the various assays.

As used herein the term "transformed" in describing host microorganism cell cultures denotes a microorganism that has been genetically engineered to produce an rIL-2 polypeptide that is capable of possessing the activity of native IL-2. Bacteria are preferred microorganisms for producing rIL-2. *E. coli* is particularly preferred.

The term "chaotropic agent" refers to a compound or compounds which, in aqueous solution and in a suitable concentration, are capable of denaturing rIL-2. Guanidine salts (e.g. the hydrochloride) and alkali metal thiocyanates (e.g., sodium thiocyanate) at concentrations in the range of about 4 to 8M, preferably about 7M, are examples of chaotropic agent solutions that will dissolve and denature rIL-2. An alternative and less preferred chaotropic agent is aqueous urea, 4–8M.

The term "oxidized" as used to characterize rIL-2 and processes for making same intends IL-2 in which the disulfide bonding that occurs in native IL-2 is present and processes which promote such bonding without promoting disulfide bonds that do not occur in native IL-2.

B. Cell Growth

The rIL-2-producing transformed microorganisms are grown in a suitable growth medium, typically to an optical density (OD) of at least about 30 at 680 nm, and preferably between about 20 and 40 at 680 nm. The composition of the growth medium will depend upon the particular microorganism involved. The medium is an aqueous medium containing compounds that fulfill the nutritional requirements of the microorganism. Growth media will typically contain assimilable sources of carbon and nitrogen, energy sources, magnesium, potassium and sodium ions, and optionally amino acids and purine and pyrimidine bases. (See *Review of Medical Biology*, Lange Medical Publications, 14th Ed pp. 80–85 (1980).) In expression vectors involving the trp promoter, the tryptophan concentration in the medium is carefully controlled to become limiting at the time protein expression is desired. Growth media for *E. coli* are well known in the art.

After the cells are harvested from the culture, they may be concentrated, if necessary, to about 20 to 150 mg/ml, preferably 80 to 100 mg/ml (OD 40 to 300, preferably 160 to 200 at 680 nm) by cross-flow filtration, centrifugation, or other conventional methods. Preferably a compound which is non-toxic to humans, such as 1-octanol, in an amount of about 1% by weight of total components, is added to the fermenter before or during cell concentration to ensure that no viable recombinant organisms remain before cell membrane containment is broken.

C. Cell Disruption

Following concentration of the harvested culture, the cell membranes of the microorganisms are disrupted. Conventional cell disruption techniques such as homogenization, sonication, or pressure cycling may be used in this step of the process. The end point of the disruption step can be determined by monitoring the optical density, with the absorbance at 260 nm of the suspension typically increasing with cell lysis. In any event, the disruption should break substantially all of the cells so that substantially no intact cells are carried through to subsequent steps.

D. Treatment of Disruptate to Isolate Insoluble rIL-2

After the cells have been disrupted, deionized water is preferably added to the disruptate and greater than 99% by weight of the salts are removed therefrom. The salts are water-soluble materials composed of oppositely charged small molecular weight ions. The removal of these salts to reduce the ionic strength of the disruptate may be accomplished by diafiltration using deionized water to flush out the ions or by centrifuging to pellet the solids followed by resuspension in deionized water. If diafiltration is employed, preferably deionized water is continuously added such that the rate of addition of water equals the filtration rate.

After the salts are essentially removed, optionally a compound such as 1-octanol may be added to the desalted disruptate, if not added earlier, to ensure that no viable recombinant organisms remain before containment is broken. The desalted disruptate is again disrupted as described above for the initial disruption.

After redisruption, density or viscosity is increased and/or a gradient is created during centrifugation in the liquid within the disruptate by adding a material to the disruptate. There are several means to accomplish this purpose, all relying on the sedimentation characteristics of the particles by varying the density and/or viscosity of the liquid phase. One means to accomplish this goal is to add a material which increases the density of the liquid to a $\rho$ of about 1.1 to 1.3 g/ml, preferably 1.13 to 1.17 g/ml.

Materials which may be used to accomplish this density increase include a sugar or mixture of sugars, such as, e.g., sucrose, dextrose, fructose, maltose, maltotriose, and other mono-, di- or polysaccharides. Most preferably the sugar is sucrose. Alternatively, a two-phase system of materials such as, e.g., a glycerol/sucrose mixture may be used wherein the disrupted particles partition to the interface between the heavy and light phases and can be eluted by a liquid/liquid separation.

In addition, the viscosity of the liquid phase may be increased from 5 to 10 cps by any suitable means such as by adding a viscous compound such as, e.g., sucrose or glycerol thereto. Also, a gradient is created if, e.g., the particles are in a 60% aqueous glycerol suspension while the centrifuge bowl contains 80% aqueous glycerol.

The rIL-2-containing refractile bodies are separated from the cellular debris by high-speed centrifugation. By "high-speed centrifugation" is meant spinning the suspension in a centrifuge at about 10,000 to 40,000 times gravity (g), preferably about 10,000–20,000×g, for a suitable time period depending on the volume, generally about 10 minutes to 72 hours. At the end of this step, the bulk of the cellular components of the microorganisms have been separated from the rIL-2. In this regard the particle pellet or paste resulting from the centrifugation contains approximately 15–70% by weight IL-2 as determined by Lowry assay (Lowry et al, *J Biol Chem* (1951) 193:265–275).

E. Solubilization of rIL-2 rIL-2-containing particle pellet or paste is solubilized by mixing it with a neutral aqueous buffer containing a solubilizing agent and a reducing agent. Surfactants (detergents) which have a suitable hydrophobic-hydrophilic balance to solubilize the rIL-2 may be used as solubilizing agents. Alkali metal sulfates containing 10 to 14 carbon atoms and alkali metal alkyl sarcosinates are preferred solubilizing agents, with SDS and sarcosyl being particularly preferred. Optionally, the aqueous buffer can also contain a chelating agent in a concentration of from 3 to 7 mM. EDTA at a concentration of 5 mM is a preferred chelating agent.

The amount of solubilizing agent used in the solubilization will depend upon the particular agent. When SDS or sarcosyl is used, the preferred concentration (w/v) of SDS/sarcosyl is 0.1% –10% in buffer such as PBS (50 mM sodium phosphate, pH 7, 0.9% sodium chloride). Preferably the range of SDS would be from 2% to 7%, most preferably 5%. The solubilizing medium also contains a sufficient amount of reducing agent to prevent the solubilized rIL-2 from undergoing oxidation to any significant degree. Protein reducing agents such as DTT and 2-mercaptoethanol may be used for this purpose. The concentration of reducing agent such as DTT in the medium will usually range between about 5 to 30 mM, preferably about 20 mM. The solubilization will typically be carried out at temperatures in the range of 20° C. to 25° C. with mixing. Optionally, a reduction step may be carried out at this point. The pH, if necessary, may be adjusted to a range of 8 to 9, most preferably approximately 8.5. The suspension may be heated to 50°±5° C. for 5 to 15 minutes under nitrogen. The reaction mixture is then cooled to approximately 25° C.

The solubilization is considered complete when the sample has sat 15 minutes or the solution turns translucent. Optionally at this point, the insoluble material may be separated by centrifugation or filtration after completing the solubilization.

F. Removal of Reducing Agent

The next step in the process is to remove the reducing agent from the solubilized rIL-2 so that the solubilized rIL-2 may be oxidized. Gel filtration is a preferred way of removing the reducing agent. Gels that are capable of providing the degree of resolution required to separate the reducing agent from the solubilized rIL-2 are commercially available. When DTT is used as the reducing agent, Sephacryl ®S-200 is a preferred gel. The gel filtration will typically be run in buffered solutions (pH 5.5 to 7.0) containing about 0.1% to 1.0% solubilizing agent. The gel column will be sized to permit suitable resolution of the components.

Diafiltration may be used as an alternative to gel filtration to remove the reducing agent.

G. Oxidation of rIL-2

The rIL-2 is next subjected to a controlled oxidation. Preferred controlled oxidation procedures are described in commonly owned U.S. Pat. Nos. 4,572,798 (using an oxidation promoter containing a $Cu^{+2}$ cation such as from $CuCl_2$, $Cu(NO_3)_2$, etc) and 4,530,787 (using o-iodosobenzoic acid), the disclosures of which are incorporated herein by reference. The $Cu^{+2}$ oxidation comprises reacting the aqueous solution of rIL-2 at a pH between about 5.5 and 9, preferably 6 to 8, and most preferably about 7.5, in the presence of air with at least an effective amount of an oxidation promoter containing a $Cu^{+2}$ cation. Controlled oxidation causes the formation of disulfide bringing in the rIL-2 which conforms to the bridging in native IL-2 with no or minimal overoxidation and formation of nonconforming bridging or oligomers. Such oxidation enables the production of high yields of the recombinant IL-2 with the proper disulfide bridging.

The amount of oxidant or oxidation promoter employed is at least an effective amount for oxidation, i.e., an amount which at minimum will be necessary to conduct the oxidation reaction effectively within a convenient period of time. An effective amount is the amount approximately equivalent to the concentration of free sulfhydryl groups in the rIL-2 which are destined to be involved in forming the desired disulfide bonds. Preferably, the amount of $CuCl_2$ will range from about 5 to 275 micromolar. In the case of o-iodosobenzoic acid the mole ratio of oxidant to rIL-2 will preferably be in the range of about 0.05:1 to about 5:1, most preferably about 0.8:1 to about 2:1. The concentration of rIL-2 in the reaction mixture is kept low, i.e., generally less than about 5 mg/ml, preferably about 0.05 to about 2 mg/ml, and more preferably about 0.1 to about 1 mg/ml, to reduce the likelihood of oligomer formation. The pH is maintained between 5.5 and 9, preferably between 7 and 8 in the o-iodosobenzoic acid oxidation.

The temperature used in the oxidation will normally be between about 20° C. and 40° C., conveniently room temperature. For $Cu^{+2}$ oxidation, increasing the reaction temperature increases the rate of reaction. The oxidation reaction may be effectively terminated by, e.g., lowering the pH to a level at which the reaction ceases, freezing the solution, or adding chelators such as EDTA to the reaction mixture. Oxidation time will normally be in the range of about 4 hr to about one day.

H. Purification of Oxidized rIL-2

Following oxidation, the rIL-2 is purified to remove endotoxins to a level that meets clinical specifications (i.e., less than about 0.1 ng endotoxin per mg of rIL-2). The IL-2 is also preferably purified to remove pyrogens so as to be substantially free of pyrogens as measured by the U.S. P. rabbit pyrogen test at a dosage of $1.0 \times 10^3$ units/kg, preferably $3.3 \times 10^5$ units/kg. RP-HPLC is a preferred method for effecting such purification. Supports (stationary phases) that provide good resolution of proteins may be used in the RP-HPLC purification. C-4, C-8, or C-18 on 300 angstrom pore-size supports are examples of preferred stationary phases. The separation is carried out at an acidic pH of less than about 2.3, usually 2.1 to 2.3. The solution of oxidized rIL-2 is loaded into the RP-HPLC column and is adsorbed onto the stationary phase. A gradient solvent system comprising an organic acid, such as acetic acid or trifluoroacetic acid, and organic solvent, such as 2-propanol or acetonitrile, is used to elute the rIL-2 from the column. Acetic acid-propanol, trifluoroacetic acid-propanol, and trifluoroacetic acid-acetonitrile are preferred solvent systems. The elution conditions are similar to those described in U.S. Pat. No. 4,569,790, the disclosure of which in this regard is incorporated herein by reference.

I. Renaturation of RP-HPLC Purified rIL-2

The RP-HPLC pool may be used directly in the renaturation step, or the rIL-2 may first be recovered as a "paste" from the pool by adding a neutral aqueous buffer, such as phosphate buffered saline (PBS), to the pool, allowing precipitation to occur, and recovering the solids by centrifugation.

The pool or paste is combined with an aqueous solution of a chaotropic agent present at a concentration that causes the rIL-2 to be denatured. The chaotropic agent is preferably in an aqueous buffer, preferably PBS, at pH about 5 to 9, preferably about 7. Adjustment of pH, if necessary, may be accomplished by the addition of base such as NaOH. The amount of pellet/paste in the chaotropic agent solution will normally be in the range of 0.1 to 100 mg/ml, preferably 0.5 to 60 mg/ml. The denaturation step is typically carried out at temperatures in the range of about 4° C. to about 25° C., preferably 4° C. to 10° C., with mixing. The denaturation will typically be complete after about 5 to about 15 min of mixing. A solid, which is believed to be mainly residual solubilizing agent (SDS), is formed during the denaturation. This solid is removed from the solution by filtration or other conventional solid liquid separation techniques. The rIL-2 is then renatured from the filtered chaotropic agent solution by reducing the concentration of chaotropic agent and protein concentration in the solution by diluting the solution with a neutral aqueous buffer or by dialysis or diafiltration against a neutral aqueous buffer. The protein concentration during renaturation will normally be in the range of 0.1 to 2.5 mg/ml, preferably 0.5 to 1.5 mg/ml.

If an rIL-2 which does not have the cysteine residue at position 125 replaced with a neutral amino acid (such as rIL-2 having the amino acid sequence of native IL-2) is being renatured, it has been observed that a significant amount of IL-2 isomers having different disulfide bridging than native IL-2 are formed. For this reason, it is preferred to carry out this process on rIL-2s in which the cysteine residue at 125 is so replaced.

Following the renaturation, the renatured rIL-2 may be further purified by ion exchange chromatography to remove forms of the protein having isoelectric points lower than native IL-2, as well as other impurities. Cation exchangers may be used for this purpose which bind rIL-2 at a pH of about 6 to 7.5. Carboxymethyl agarose columns (e.g., Pharmacia Fast Flow CM Sepharose) are preferred preparative cation exchangers. The solution of renatured rIL-2 is contacted with the exchanger at the indicated pH range and the rIL-2 is eluted from the exchanger using an ionic gradient. The desired rIL-2 elutes at approximately 0.1M salt with the lower isoelectric point forms of the protein eluting at lower salt concentrations.

The renatured, oxidized rIL-2 is substantially pure (i.e., it is normally at least 95% pure, more usually at least 98% pure as measured by SDS-PAGE analysis); has an endotoxin content of less than about 0.1 ng/mg of rIL-2; is preferably substantially free of pyrogens as measured by the U.S.P. rabbit pyrogen test at a dosage of $1.0 \times 10^3$ units/kg; has a solubility in PBS of at least about 5 mg/ml; is stable in the sense that it does not aggregate in PBS at those concentrations; contains no detectable solubilizing agent (SDS) as measured by acridine orange assay and ion chromatography; and exhibits a specific activity normally in the range of $5 \times 10^6$ to $2 \times 10^7$ units/mg).

J. Formulation

The purified IL-2 is formulated in aqueous solution at a concentration in the range of about 0.01 to 2 mg/ml. A water-soluble carrier is added to the desired level. The carrier will typically be added such that it is present in the solution at about 1% to 10% by weight, preferably about 5% by weight. The exact amount of carrier added is not critical. Conventional solid bulking agents that are used in pharmaceutical tablet formulation may be used as the carrier. These materials are water soluble, do not react with the rIL-2, and are themselves stable. They are also preferably non-sensitive to water (i.e., nonhygroscopic). Specific examples of carriers that may be added include dextrose, lactose, mannitol, and other reduced sugars such as sorbitol, starches and starch hydrolysates derived from wheat, corn, rice, and potato, microcrystalline celluloses, and albumin such as human serum albumin. Mannitol and dextrose are preferred.

The carrier adds bulk to the formulation such that when unit dosage amounts of the solution are lyophilized in containers, such as sterile vials, the freeze-dried residue will be clearly discernible to the naked eye. In this regard the preferred carrier, mannitol, yields an aesthetically acceptable (white, crystalline) residue that is not sensitive to water. The nonsensitivity of mannitol to water may enhance the stability of the formulation.

EP publication 215,658, published 25 Mar. 1987, entitled "An Improved Formulation for Lipophilic Proteins" (Hanisch et al) outlines an improved process for recovering and purifying lipophilic recombinant proteins such as rIL-2 from microorganisms to yield a protein preparation which may be formulated into a stable pharmaceutical composition. Such a composition carrying a therapeutically effective amount of the biologically active recombinant lipophilic protein dissolved in a non-toxic, inert, therapeutically compatible aqueous-based carrier medium at a pH of 6.8 to 7.8 also contains a stabilizer for the protein, such as human serum albumin, normal serum albumin and human plasma protein fraction. The formulation aspects of said EP publication 215,658 are herein incorporated by reference as an alternative formulation route for the purified IL-2. EP publication 215,658 outlines a low pH formulation process. U.S. Pat. No. 4,462,940 to Hanisch et al, outlines a high pH formulation process, and the formulation aspects thereof are also herein incorporated by reference.

After adding the carrier, the unit dosage amounts (i.e., for rIL-2 volumes that will provide 0.01 to 2 mg, preferably 0.2 to 1.0 mg, rIL-2 per dose) of the solution are dispensed into containers, the containers are capped with a slotted stopper, and the contents are lyophilized using conventional freezedrying conditions and apparatus.

The lyophilized, sterile product consists of a mixture of (1) rIL-2, (2) carrier (dextrose or mannitol), (3) optionally other excipients such as human serum albumin, Tween 80, and the like, and (4) a small amount of buffer that will provide a physiological pH when the mixture is reconstituted. The product may also contain a minor amount of a preservative to enhance chemical stability. The rIL-2 will typically constitute about 0.015% to 3.85% by weight of the mixture, more preferably about 0.4% to 0.6% of the mixture.

The lyophilized mixture may be reconstituted by injecting a conventional parenteral aqueous injection such as distilled water for injection, Ringer's solution injection, Hank's solution injection, dextrose injection, dextrose and salt injection, physiological saline injection, or the like, into the vial. The injection should be added against the side of the vial to avoid excess foaming. The amount of injection added to the vial will typically be in the range of 1 to 5 ml, preferably 1 to 2 ml.

In an alternative formulation, described in PCT WO87/00056, published 15 Jan. 1987, entitled "Solubilization of Recombinant Proteins for Pharmaceutical Compositions Using Homopolymer Conjugation" to M. Knauf et al, the disclosure of which is incorporated herein by reference, the IL-2 is reacted with an activated polymer selected from polyethylene glycol homopolymer and poly-oxy-ethylated polyols such as polyoxyethylated glycerol. The polymer preferably has a molecular weight of from 300 to 100,000 daltons, more preferably 350 to 40,000 daltons. The polymer is activated by conjugation with a coupling agent having terminal groups reactive with both the free amine or thiol groups of the protein and the hydroxyl group of the polymer. Examples of such coupling agents include hydroxynitrobenzene sulfonic ester, cyanuric acid chloride, and N-hydroxy-succini-mide. The rIL-2 is then formulated directly with the water-soluble carrier and buffer as described above, the formulation is lyophilized, and the lyophilized mixture may be reconstituted as described above.

The reconstituted formulation prepared as described above is suitable for parenteral and oral administration to humans or other mammals in therapeutically effective amounts (i.e., amounts which eliminate or reduce the patient's pathological condition) to provide therapy thereto. rIL-2 therapy is appropriate for a variety of immunomodulatory indications such as T cell mutagenesis, induction of cytotoxic T cells, augmentation of natural killer cell activity, induction of IFN-$\gamma$, restoration and enhancement of cellular immunity (e.g., treatment of immune deficient conditions), and augmentation of cellmediated anti-tumor activity.

The formulations of this invention are useful for parenteral administration, for example, intravenous, subcutaneous, intramuscular, intraorbital, ophthalmic, intracapsular, intraspinal, intrasternal, topical, intranasal aerosol, scarification, and also, for oral administration. The preferred routes of administration are by intramuscular, subcutaneous and intravenous injection, and by topical administration. The use of nonionic detergents are especially preferred for topically administered formulations because of their ability to penetrate the skin surface.

The following examples further illustrate the invention. These examples are not intended to limit the invention in any manner. In these examples all temperatures are in degrees Celsius unless otherwise indicated.

EXAMPLE 1

This example illustrates a preferred process for recovering, purifying, renaturing, and formulating rIL-2 from *E. coli*.

Des-alanyl-IL-2$_{ser125}$ was recovered from *E. coli*. The strain of des-alanyl-IL-2$_{ser125}$-producing *E. coli* (K12/MM294-1) carrying plasmid pLW45 used in this example was deposited at the American Type Culture Collection of 4 Mar. 1984 under accession number 39,626. Said analog is disclosed in U.S. Pat. No. 4,518,584 and prepared by the methods disclosed in U.S. Pat. No. 4,518,584 assigned to Cetus Corporation.

The *E. coli* thus transformed with plasmid pLW45 were grown in a 1000-liter fermenter at 37° C. The dissolved oxygen was maintained at about 40% by, as necessary, (1) increasing agitation; (2) adding air; and (3) adding oxygen.

Once the fermenter was filled with water to the operating volume, the following trace elements were added:

$ZnSO_4 \cdot 7H_2O$: 30 $\mu$M
$MnSO_4 \cdot 4H_2O$: 30 $\mu$M
$CuSO_4 \cdot 5H_2O$: 3 $\mu$M
$Na_3$ citrate $\cdot 2H_2O$: 1.5 mM
$KH_2PO_4$: 21 mM
$(NH_4)_2SO_4$: 72 mM.

The fermenter feed and addition vessels were then sterilized according to standard operating procedures. Then the following sterile additions were made:

$MgSO_4 \cdot 7H_2O$: 3 mM
$FeSO_4 \cdot 7H_2O$: 72 $\mu$M
L-tryptophan: 70 mg/L
thiamine·HCl: 20 mg/L
glucose: 5 g/L
tetracycline: 5 mg/L.

The fermenter was cooled and inoculated with frozen or seed *E. coli* culture at 2 mg/L. A glucose feed was employed to maintain the glucose concentration between 5-10 g/L. At approximately 15 hours after fermentation was begun, the pH was adjusted with KOH to 6.8. Optical density measurements and residual glucose measurements on samples were taken at 14-16 hours and approximately one hour intervals thereafter.

Induction of des-alanyl-IL-2$_{ser125}$ production by depletion of L-tryptophan from the culture medium occurred at about $OD_{680}=10$ followed by the addition of casamino acids to a final concentration of 2% at $OD_{680}=15$. Cultures were harvested about 3-5 hours later.

The refractile bodies containing the desalanyl-IL-2$_{ser125}$ were then isolated. The harvested material was concentrated about 5-10 fold by circulating the harvest material under pressure through UF cross-flow filtration cartridges with a 100K molecular weight cutoff. The cells were washed with deionized water. EDTA was added to 25 mM, and the cells were disrupted by 3 passes through a disruptor at about 6500 psi (195 atm).

After the suspension was diafiltered against 5 volumes of deionized water, EDTA was added to a final concentration of 5 mM. Octanol was added to 1% (v/v) to kill any residual live bacteria in the diafiltered product. After several hours, the diafiltered disruptate was redisrupted by passing it through a disruptor.

Sucrose was added to the redisruptate to create a final density between 1.1 and 1.25 g/ml. The mixture was centrifuged at 10,000 to 20,000 $\times$ g at 1-2 1 pm, and the particle pellet or paste was collected. A temperature of at least 20° C. was maintained prior to and during centrifugation.

The particle paste was then solubilized in PBS with 5% SDS. The solubilized paste was then centrifuged at 25,000-35,000 $\times$ g.

Solid DTT and EDTA were added to a final concentration of 50 mM and 2 mM, respectively. The suspension was heated to 50° ±5° C. for 20 min under nitrogen at a pH of about 8.5. The reaction mixture was then cooled to approximately 25° C., and then the pH of the mixture was re-adjusted to 5.5±0.1 using glacial acetic acid.

Chromatographic separation of the higher molecular weight contaminants was achieved using a Sephacryl ™ S-200 column. The solubilized and reduced rIL-2 was loaded onto the column and fractions were collected into clean, depyrogenated vessels using an elution buffer containing 50 mM acetate pH 5.5, 1 mM EDTA and 0.1% SDS. Peak fractions (those falling within 70% of the maximum peak height) were pooled and subjected to a controlled oxidation as follows:

Oxidation of the rIL-2 in the S-200 pool was initiated by adding $CuCl_2$ in a molar ratio of 3:1 ($CuCl_2$ to rIL-2). The oxidation was carried out at about 25° C. in 50 mM phosphate buffered saline. The pH was controlled at 7.5±0.2 during oxidation and 4 mM EDTA was added when the oxidation was completed. Since oxidized rIL-2 is more hydrophilic than reduced rIL-2, the progress of the oxidation reaction was monitored by RP-HPLC.

The oxidized IL-2 was then concentrated using a hollow fiber ultrafiltration unit with a 10,000 dalton molecular weight cutoff. The pH of the oxidized pool was then adjusted to pH of about 2 to about 3 and filtered through a 0.45µ nitrocellulose filter.

Preparative HPLC using a Vydac ® $C_4$ bonded phase silica gel column supplied with two solvents was the next step in the rIL-2 purification scheme. Solvent 1 was 6% acetic acid and 10% 2-propanol, and solvent 2 was 6% acetic acid and 94% 2-propanol. After pumping solvent 1 for 30 minutes, the acidified rIL-2 was loaded. The column was developed with a gradient of solvents 1 and 2 and the protein which eluted at about 40% solvent 2 was pooled into a depyrogenated graduated cylinder. Phosphate buffer was added to the pool to neutralize pH resulting in the formation of a precipitate ("HPLC paste") which was recovered by centrifugation.

Alternatively a trifluoroacetic acid-acetonitrile solvent system using an acetonitrile gradient as described in U.S. Pat. No. 4,569,790 may be used in the preparative HPLC.

Small-scale renaturation of rIL-2 from the HPLC paste was carried out by dissolving the paste in 7M guanidine buffer. The solution was filtered through a 0.2 micron filter and then dialyzed using 6-8 kd cut-off cellulose dialysis tubing into 20 mM sodium phosphate buffer, pH 7.4 or Tris, pH 8.1.

Large scale renaturation of rIL-2 from the paste was carried out as follows. Approximately one gram of HPLC paste was washed and repelleted two times with 100 ml of 0.1M sodium phosphate buffer (pH 6.0). The pellet was dissolved in 100 ml of 7M guanidine (10 mM sodium phosphate buffer). Fine particles were removed by adding several spatula scoops of Celite and filtering through a 0.2 micron filter. An additional 600 ml of guanidine buffer was added to the filtered solution and it was then diafiltered with a 1 square foot YM-10 spiral cartridge (Amicon). Cold sodium phosphate (10 mM, pH 7.0) with 2.5% sucrose was used for the exchange buffer. The diafiltration rate was approximately two volume changes per hour. After 6 volume changes a cloudy solution was obtained which was filtered through a 0.2 micron Nalgene flat filter with a prefilter insert. A yield of 80% (800 ml, 1.12 mg/ml) was obtained.

Preparative chromatography performed on the diafiltered HPLC solubilized paste was done on Pharmacia Fast Flow Carboxylmethyl (CM) Sepharose. Buffers used for gradient elution were pH 7.0 sodium phosphate buffer and sodium phosphate buffer with sodium chloride added. rIL-2 was recovered at 0.1M salt concentration.

In the small scale renaturation using dialysis, about 85% of the original protein consistently remained in solution after removal of guanidine. This yield remained consistent over a range of protein concentration of 0.3 to 1.5 mg/ml. An acridine orange assay indicated that there was essentially no SDS left after solubilization, filtration and dialysis of the HPLC paste. Residual SDS present in the HPLC paste appeared to precipitate following solubilization of the rIL-2 in guanidine hydrochloride and was apparently removed by filtration.

Figure 2:
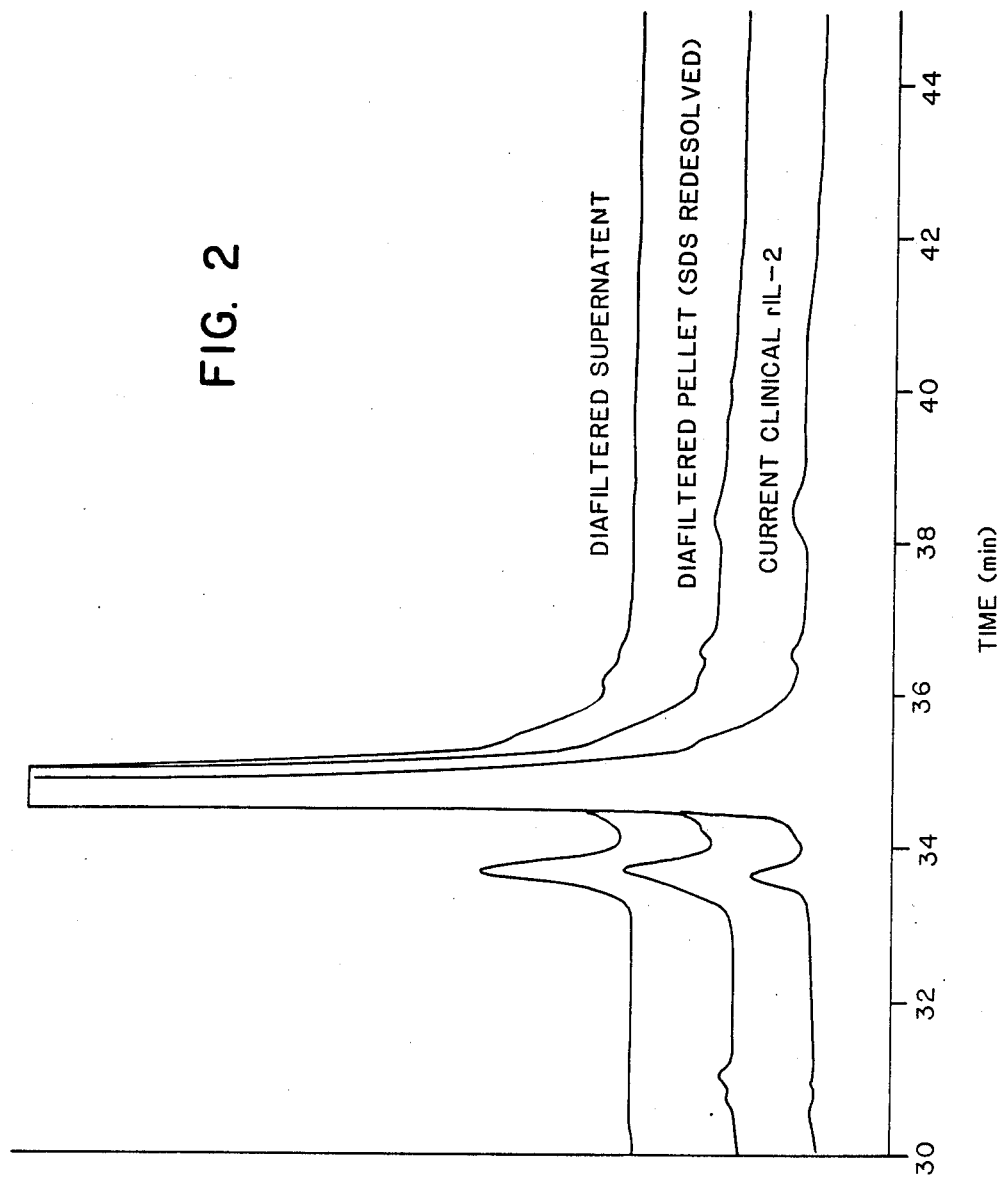
FIG. 2 is an RP-HPLC chromatogram of materials described in Example 1, infra.

The protein that precipitated during the dialysis could be resolubilized with 7M guanidine and redialyzed. However, less than 15% of the protein is recovered as a soluble product. FIG. 2 is an RP-HPLC chromatogram for diafiltered supernatant, diafiltered pellet, and a current clinical rIL-2 product produced generally by the process described in U.S. Pat. Nos. 4,569,790 and 4,572,978. This figure shows that the material that failed to renature is very similar to the protein that remains soluble after dialysis. The activity of both the renatured and nonrenaturable materials is similar, both being approximately $10^7$ units/mg.

The small scale dialysis renaturation was very well reproduced with diafiltration equipment and demonstrates that the procedure can be carried out on a large scale with no significant difficulties. Sucrose was added to the exchange buffer to help prevent precipitation of the rIL-2 due to agitation. The precipitation which occurred during the diafiltration caused no significant reduction in the rate of diafiltration. The SDS concentrations after diafiltration were again not detectable.

Figure 3:
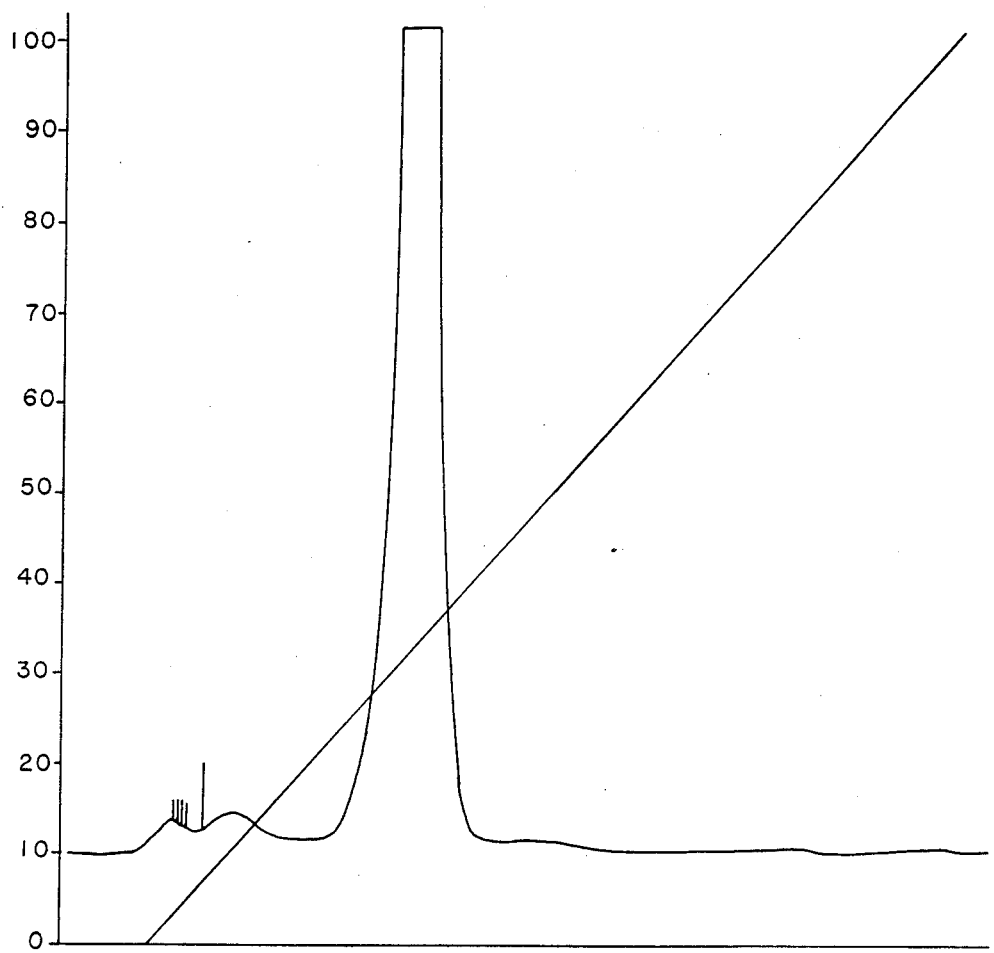
FIG. 3 is a Fast Flow CM chromatogram of materials described in Example 1, infra.

Preparative chromatography on a column of Fast Flow CM Sepharose (FIG. 3) was able to separate some of the minor forms of IL-2 from a main peak. Up to 87% of the material applied to the preparative column was recovered as the main peak. In order to obtain this high yield it was necessary to have the initial salt concentration of the A buffer and the concentration at least 40 to 50 mM. Lower salt concentrations cause significantly lower yields.

EXAMPLE 2

This example further illustrates the advantages of renaturing purified, oxidized rIL-2 prepared by the prior art processes.

rIL-2 was prepared as in Example 1 up through obtaining an RP-HPLC pool. Pooled protein was diluted by slowly adding it to a stirred buffer solution containing 50 mM sodium acetate pH 5.5, 1 mM EDTA and 0.1% SDS that had 14 times the volume of the HPLC pool. Dilution was required due to the sensitivity of the hollow-fiber ultrafiltration unit used for concentration in the next step to the organic solvents present in the HPLC pool.

The diluted HPLC pool was concentrated using a hollow-fiber ultrafiltration unit with a 10,000 molecular weight cutoff. The concentrate was diafiltered against 50 mM acetate pH 5.5, 1 mM EDTA and 0.1% SDS with three volume exchanges.

The final chromatographic step in the purification of rIL-2 involved a second Sephacryl ® S-200 column.

The primary objective of this column was to separate the rIL-2 from higher molecular weight oligomers of the protein. The column was eluted with buffer containing 50 mM acetate, pH 5.5, 1 mM EDTA and 0.1% SDS, and rIL-2 fractions were pooled. The protein was diafiltered against 10 mM sodium phosphate, pH 7.5 until the SDS level was in the range of 100–200 μg/mg protein.

Eight milligrams of the post-diafiltered IL-2 was purified on a C4 Vydac ® RP-HPLC column run in acetonitrile/TFA following addition of SDS to 0.1% w/v. The RP-HPLC pool was dialyzed into 7M guanidine and then dialyzed extensively into 0.1M phosphate buffer (pH 7.0). A small amount of precipitate formed in the rIL-2 which was removed by centrifugation for 10 min at 15,000×g. The yield of soluble rIL-2 was 80% (6.4 mg). This material was further analyzed using (1) a spectral assay for aggregation, (3) molecular sizing in phosphate buffer, and (3) bioactivity. The results are described below.

Spectral Assay

Figure 4:
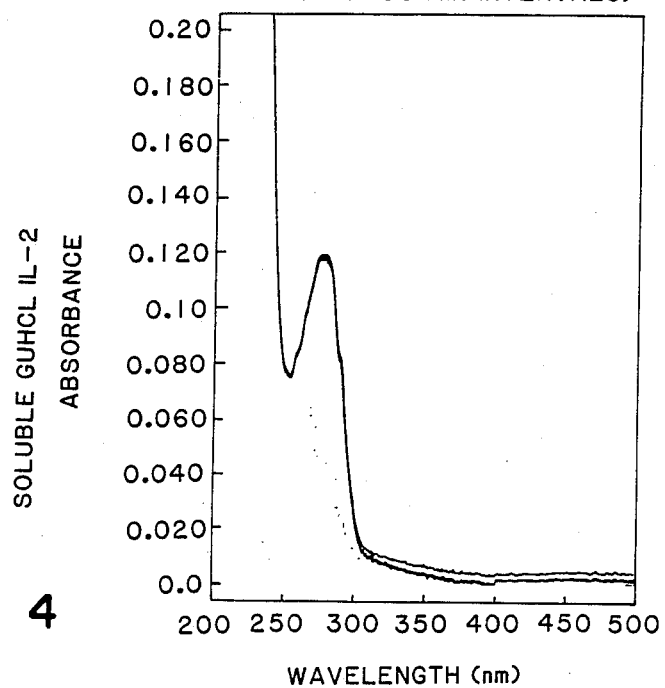
FIG. 4 is a set of UV spectra of phosphate buffered saline (PBS) dilutions of rIL-2 preparations described in Example 2, infra.
Figure 4:
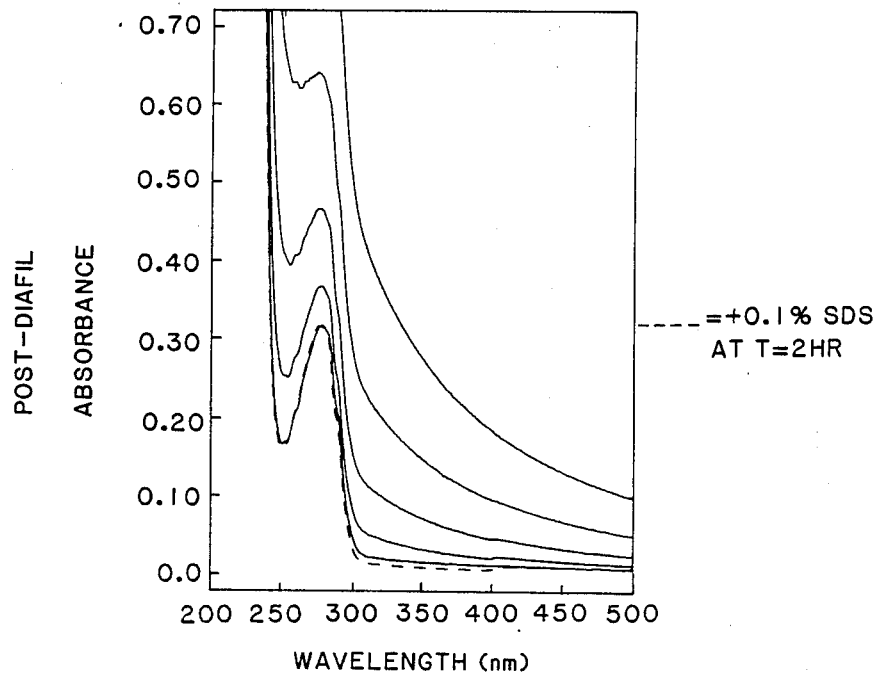

The UV spectrum of rIL-2 changes depending on the apparent state of aggregation of the molecule. This physical parameter was used to compare rIL-2 formulations following a five-fold dilution into 10 mM sodium phosphate, 150 mM sodium chloride, pH 7.4. Spectral scans were recorded over a period of 2 hr at 30-min intervals immediately following dilution. As shown in FIG. 4, panel A, the guanidine-renatured rIL-2 appears stable under these conditions with no change in absorbance at 280 nm. In contrast, post-diafiltered rIL-2 (panel B) aggregates during the course of the assay, demonstrating its reduced solubility following a decrease in SDS concentration. As a control, 0.1% SDS was added back to the post-diafiltered rIL-2 t=2 hr after the 5-fold dilution, and as can be seen in panel B (dashed line), the rIL-2 spectrum returns to normal; indicating that the absence of SDS was the cause of this reversible aggregation.

Molecular Sizing

Figure 5:
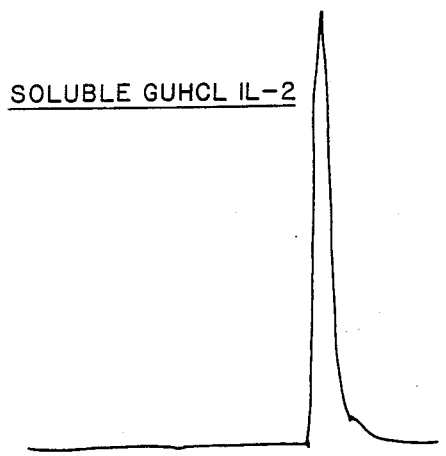
FIG. 5 is a set of HPLC chromatograms from the molecular sizing experiments described in Example 2, infra.
Figure 5:

The recovery of SDS-formulated rIL-2 following molecular sizing HPLC analysis is not high, presumably due to aggregation and subsequent loss on the frits and column. However, when the renatured rIL-2 was analyzed by this method, recoveries were greatly increased. As shown in FIG. 5, the renatured rIL-2 elutes as a large, symmetrical peak with an apparent molecular weight of about 16 kd. When an equal amount of post-diafiltered rIL-2 was analyzed, a small, assymetrical peak was obtained, indicating that the rIL-2 did not remain in solution in physiological buffers.

Biological Activity

The specific activity of the renatured rIL-2 was determined to be about $1.5 \times 10^7$ μ/mg as measured by the HT-2 cell proliferation assay.

In addition to the aforedescribed vector system employing the trp promoter for IL-2 expression, alternative vector systems include the use of the lambda pL promoter and/or a positive retroregulatory element. These vector systems are described in U.S. Pat. Nos. 4,711,845, issued 8 Dec. 1987 and 4,666,848, issued 19 May 1987, the disclosures of both are incorporated herein by reference.

Vector systems described in the aforedescribed patents, as well as additional vectors provided below, have been deposited with the American Type Culture Collection (ATCC), 12301 Parklawn Drive, Rockville, Md. under the terms of the Budapest Treaty on the International Recognition of the Deposit of Microorganism for the Purpose of Patent Procedure and Regulations thereunder and are thus maintained and made available according to the terms of the Budapest Treaty. Availability of such strains is not to be construed as a license to practice the invention in contravention of the rights granted under the authority of any government in accordance with its patent laws.

The deposited plasmids have been assigned the indicated ATCC deposit numbers:

| Plasmid | ATCC No. | Deposit Date |
| --- | --- | --- |
| pFC54 in E. coli DG95 lambda (N₇N₅₃cI857SusP₈₀) | 39831 | 4 September 1984 |
| pFC54.t in E. coli DG95 lambda | 39789 | 31 July 1984 |
| pHCW701 in E. coli K12 MM294 | 39757 | 8 June 1984 |
| pLW1 in E. coli K12 MM294 | 39405 | 25 July 1983 |
| pLW46 in E. coli K12 MM294 | 39452 | 29 September 1983 |
| pLW55 in E. coli K12 MM294.1 | 39516 | 29 September 1983 |
| pSY3001 in E. coli K12 MM294 | 39949 | 19 December 1984 |

Modifications of the above-described modes for carrying out the invention that are obvious to those skilled in sciences and technologies related to the invention are intended to be within the scope of the following claims.

We claim:

1. In a process for recovering recombinant interleukin-2 (rIL-2) from transformed microorganisms containing the rIL-2 wherein the rIL-2 is separated from the bulk of the cellular components of the microorganisms, solubilized in a reduced form, thereafter oxidized, and thereafter purified to clinically acceptable purity and endotoxin levels, the improvement comprising denaturing the oxidized, purified rIL-2 by placing the rIL-2 in a solution of a chaotropic agent, removing solids from the solution, and thereafter renaturing the rIL-2 from the solution, whereby a renatured, oxidized, purified rIL-2 having improved stability and solubility properties in the absence of detergents is obtained.

2. The process of claim 1 wherein the solubilization of the reduced rIL-2 is achieved by mixing the separated rIL-2 with an aqueous solution from 0.1 to 10% (w/v) of sodium dodecyl sulfate.

3. The process of claim 2 wherein the solution of a chaotropic agent is a 4 to 8M aqueous guanidine hydrochloride solution.

4. The process of claim 2 wherein the solution of a chaotropic agent is an approximately 7M aqueous guanidine hydrochloride solution.

5. The process of claim 3 wherein the concentration of purified IL-2 in the aqueous guanidine solution is 0.1 to 100 mg/ml.

6. The process of claim 3 wherein the concentration of purified IL-2 in the aqueous guanidine solution is 0.5 to 60 mg/ml.

7. The process of claim 5 wherein the denaturation is carried out at 4° to 25° C.

8. The process of claim 5 wherein the pH of the aqueous guanidine solution is 5 to 9.

9. The process of claim 2 wherein the removal of solids from the solution of chaotropic agent into which the rIL-2 has been placed is effected by filtration.

10. The process of claim 2 wherein the renaturation is effected by dialysis or dilution of the chaotropic agent solution.

11. The process of claim 10 wherein the renaturation is effected at a protein concentration of 0.1 to 2.5 mg/ml.

12. The process of claim 10 wherein the renaturation is effected at a protein concentration of 0.5 to 1.5 mg/ml.

13. The process of claim 2 wherein the renatured oxidized purified rIL-2 is further purified by contacting an aqueous solution of the renatured rIL-2 with a cation exchanger at a pH of about 6 to 7.5, eluting the adsorbed fraction from the cation exchanger with a salt gradient and recovering the further purified rIL-2 at about 0.1M salt concentration.

14. The process of claim 3 wherein the renaturation is effected by dialysis, and the renatured oxidized purified rIL-2 is further purified by contacting an aqueous solution of the renatured rIL-2 with a cation exchanger at a pH of about 6 to 7.5, eluting the adsorbed fraction from the cation exchanger with a salt gradient, and recovering further purified rIL-2 at a salt concentration of about 0.1M.

15. The process of claim 1 wherein the rIL-2 is separated from the bulk of the cellular components by disrupting the cells and separating the water insoluble material from the resulting disruptate, the rIL-2 is solubilized in a reduced form by mixing said water insoluble material with an aqueous solution of sodium dodecyl sulfate that contains a reducing agent, the reducing agent is removed from the solubilized rIL-2 prior to the oxidation, the oxidation is a controlled oxidation using $Cu^{+2}$ ion as an oxidation promoter, and the oxidized rIL-2 is purified to clinically acceptable endotoxin specifications by reverse phase high performance liquid chromatography.

16. The process of claim 1 wherein the rIL-2 is purified to clinically acceptable pyrogen levels.

17. The process of claim 15 wherein the rIL-2 is purified to clinically acceptable pyrogen levels.

* * * * *